US009275534B2

(12) United States Patent
Alasaarela

(10) Patent No.: US 9,275,534 B2
(45) Date of Patent: Mar. 1, 2016

(54) METHOD AND ARRANGEMENT FOR EVALUATING ACTIVITY AND FUNCTIONAL ABILITY BASED ON INTERACTION AND PHYSIOLOGICAL SIGNALS

(75) Inventor: Esko Alasaarela, Oulu (FI)

(73) Assignee: Domuset Oy, Oulu (FI)

( * ) Notice: Subject to any disclaimer, the term of this patent is extended or adjusted under 35 U.S.C. 154(b) by 53 days.

(21) Appl. No.: 14/240,568

(22) PCT Filed: Sep. 2, 2011

(86) PCT No.: PCT/FI2011/050759
§ 371 (c)(1),
(2), (4) Date: May 13, 2014

(87) PCT Pub. No.: WO2013/030428
PCT Pub. Date: Mar. 7, 2013

(65) Prior Publication Data
US 2015/0070172 A1    Mar. 12, 2015

(51) Int. Cl.
*G08B 23/00* (2006.01)
*G08B 21/04* (2006.01)
(Continued)

(52) U.S. Cl.
CPC .......... *G08B 21/0415* (2013.01); *A61B 5/0022* (2013.01); *A61B 5/0205* (2013.01);
(Continued)

(58) Field of Classification Search
CPC ............ G06F 19/3418; G08B 21/0415; A61B 5/0022; A61B 5/0205; A61B 5/1108; A61B 5/1113
USPC ................ 340/573.1, 573.3, 573.4, 340/539.12–539.17; 600/300, 301; 348/143, 152–155, 159
See application file for complete search history.

(56) References Cited

U.S. PATENT DOCUMENTS 6,433,690 B2 *   8/2002   Petelenz et al. ............. 340/573.1
7,925,606 B1 *   4/2011   Katzer et al. ...................... 705/2
(Continued)

FOREIGN PATENT DOCUMENTS

WO        2011055004         5/2011

OTHER PUBLICATIONS

Bennett, R.P.C, et al., "Owner-companion dog interactions: Relationships between demographic variables, potentially problematic behaviours, training engagement and shared activities", Applied Animal Behavior Science, 2007, 102:65-84; available online Apr. 18, 2006.
(Continued)

*Primary Examiner* — Thomas Mullen
(74) *Attorney, Agent, or Firm* — Andrus Intellectual Property Law, LLP

(57) ABSTRACT

A method is for monitoring interaction between a person and his companion and pet. The method can be realized via a data transfer network, a monitoring arrangement used in the method, a server and a computer program to be used in the monitoring arrangements, which are included in the monitoring arrangement. With the method and monitoring arrangement, an interactive event between the companion and person and/or pet can be visualized on a data processing device for a selected time period. The data processing device can be situated in a different location than the persons and pet being monitored. In the method, the latest 3D location measuring data and physiological measuring data of the pet, companion and person are compared to long-term average data. The physiological measuring data is received from wireless monitoring devices carried by the pet, companion and person.

16 Claims, 8 Drawing Sheets

(51) Int. Cl.
*A61B 5/0205* (2006.01)
*A61B 5/11* (2006.01)
*A61B 5/00* (2006.01)

(52) U.S. Cl.
CPC .............. *A61B5/1108* (2013.01); *A61B 5/1113* (2013.01); *A61B 5/4803* (2013.01); *A61B 5/7264* (2013.01); *A61B 2503/40* (2013.01); *A61B 2562/0219* (2013.01)

(56) References Cited

U.S. PATENT DOCUMENTS

| | | | |
|---|---|---|---|
| 2002/0135484 A1* | 9/2002 | Ciccolo et al. | 340/573.1 |
| 2002/0171551 A1* | 11/2002 | Eshelman et al. | 340/573.1 |
| 2004/0021569 A1* | 2/2004 | Lepkofker et al. | 340/539.13 |
| 2005/0119532 A1* | 6/2005 | Cloutier | 600/300 |
| 2006/0011144 A1 | 1/2006 | Kates | |
| 2006/0293570 A1* | 12/2006 | Croghan et al. | 600/300 |
| 2007/0265533 A1* | 11/2007 | Tran | 600/481 |
| 2008/0084296 A1* | 4/2008 | Kutzik et al. | 340/540 |
| 2008/0183049 A1* | 7/2008 | Karkanias et al. | 600/301 |
| 2009/0326339 A1* | 12/2009 | Horvitz | 600/301 |

OTHER PUBLICATIONS

Marti, P. et al., "Socially Assistive Robotics in the Treatment of Behavioural and Psychological Symptoms of Dementia," The First International Conference on Biomedical Robotics and Biomechatronics, Feb. 20, 2006.

Waiblinger, S. et al., "Assessing the human-animal relationship in farmed species: A critical review", Applied Animal Behavior Science, Dec. 15, 2006.

International Search Report for PCT/FI2011/050759, dated Jun. 5, 2012.

* cited by examiner

METHOD AND ARRANGEMENT FOR EVALUATING ACTIVITY AND FUNCTIONAL ABILITY BASED ON INTERACTION AND PHYSIOLOGICAL SIGNALS

CROSS-REFERENCE TO RELATED APPLICATIONS

This application is the U.S. national stage application of International Application PCT/FI2011/050759, filed Sep. 2, 2011, which international application was published on Mar. 7, 2013, as International Publication WO2013/030428 in the English language. The international application is incorporated herein by reference, in entirety.

FIELD

The invention relates to a method for monitoring activity and functional ability of a person, persons and/or a pet. The invention also relates to an arrangement for monitoring and evaluating activity and functional ability and to a server utilised in the monitoring of the activity and functional ability and to a computer program used in the monitoring of the activity and functional ability.

BACKGROUND

The elderly portion of the population grows quickly in industrialised countries. An elderly person often lives in a place, where relatives or friends do not have time to visit sufficiently often in order to evaluate the health and functional ability of the person. In such a case the worry of the relatives and friends for how the person they are close to manages in their daily routines can be great.

In order to eliminate such a situation, various computerised solutions have been developed, by using which the daily activities of a person or several persons can be monitored on a rough level. The apartment, which a person uses, can for example be equipped with various door or room sensors, which indicate the use of the door or the movement of the person inside the room. Thus the person's movement can be discovered over a certain time period. If no signals regarding the person's movement are received from the sensors either at a certain time or at certain time intervals, the arrangement provides an alarm, which is relayed through a data network. Examples of such monitoring systems are shown in the patents JP 2007299121 and CN 101324662.

Solutions are also known, wherein the person has a device for example on his or her wrist, which device monitors vital functions or which can be used to send an alarm to an external person in situations, where the person feels that his or her ability has weakened. The alarm can be sent for example via radio, telephone or the internet.

Owning and caring for pets also continuously becomes more common. Caring for pets is an element, which counterbalances the daily hustle for a busy human. The presence of a pet has also been shown to be beneficial for a human's mental welfare and even to lower the blood pressure. Doing things with a pet maintains both the physical and mental fitness of a person.

Various pet monitoring and controlling means functioning via data networks are known. Especially the emergence and development of the internet as a central communication channel has made the development of various pet monitoring and controlling systems easier. With such monitoring and controlling means the behaviour of a pet can be monitored in real-time either via video image or an audio dispatch also when outside the home. From the video images and/or the sounds of the pet one can deduce in what kind of activity state the pet is at that exact moment.

The movement and recreation of the pet can also be monitored in real-time via a data network. The locationing of the pet in the home can be implemented for example with video surveillance, RFID identifier readers, GPS, infrared sensors, acoustic locationing methods, ultrasound locationing, radio locationing or calculation of the location based on acceleration measurement.

At least part of the monitoring of the daily activities of the pet can be given over to a suitably programmed home computer. In such a system a computer in the home simulates the owner during at least a part of the day. One such arrangement is depicted in application publication US 2006/0011144. The depicted arrangement comprises real-time positioning of a pet (dog) with various methods, control of the food and drink dispensers, monitoring of the activity state of the dog with an acceleration sensor (in its place or moving), monitoring of the body temperature of the dog, monitoring of the barking of the dog, creating various scent, sound and picture animations depicting the owner and showing them to the dog. If an activity model, which differs from the normal, can be observed in the activity of the dog at a certain time, the computer sends an alarm regarding the matter to the dog owner. The solution shown in the reference publication can thus give an alarm, if the activity of the dog momentarily differs sufficiently from activity models stored in the memory of the computer.

The arrangement shown in reference publication US 2006/0011144 cannot make conclusions in situations, where the activity of a dog surprisingly changes, even if the activity stays within normal limits, but the movement of the dog still changes either temporarily or little by little to differ completely from the normal movement. For example the dog moves as much as before, but the movement area has changed from the usual. One possibility of the movement of the pet changing in the described manner is a sudden change in the functional ability of a person in the apartment, such as for example a sudden illness.

SUMMARY

It is an object of the invention to present an arrangement, which can use data obtained via long-term monitoring regarding a person's activity and physiological measurements and from interaction between the person in question and his companion, for example a pet or a living companion of the person being monitored. Physiological measuring data of the subjects being monitored and monitoring data related to mutual interaction, such as distance between locations and dependence of movement on each other, are especially utilised. By comparing short-term monitoring results to the long-term monitoring results, changes related to physiological measurements and mutual behaviour of the targets being monitored, the person and his companion and/or pet, which changes do not appear simply from short-term monitoring results, can be discovered.

The objects of the invention are attained with a system, where movement measuring and other momentary movement, vital function and behaviour data obtained with sensors attached to the person being monitored and the companion, such as living companion or pet, is compared to corresponding long-term measuring data of the person and companion or pet being monitored in order to perceive a possible problem related to the health or functional ability of the person being monitored.

An advantage of the invention is that by combining the vital function measuring data of the person being monitored, his companion and pet, a situation, which does not appear simply from the measuring data of a single target being monitored, can be indicated in the changes in behaviour and movement of the person, companion and/or pet.

An advantage of the invention is further that a data network can for analysis of the problem be used for visualising to relatives or friends (persons performing monitoring) the movement of both the person being monitored, the companion and the pet in the apartment during a time period selected by the person performing the monitoring. In the visualisation of the movement the location of the resting place of the person, the companion, such as living companion or pet, can be used as starting information, a kind of calibration information, when the person, companion or pet starts moving after resting.

It is a further advantage of the invention that all other activities and vital function measuring data discovered during the movement of the person, companion and/or pet can be visualised at their occurrence locations. This helps in the interpretation of the measuring data to avoid faulty conclusions and unnecessary contacts. For example if the monitoring target is in the middle of the day unmoving for a long time, but the monitoring system indicates that he is in his own bed and the activity and vital functions of the companion are at a normal level, it may be surmised that the monitoring target is taking a nap. On the other hand if the monitoring target is unmoving in some unusual place and the activity and vital functions of the companion, such as living companion or pet, are based on physiological measuring results accelerated, there is cause to make contact by telephone and ask about the wellbeing of the person being monitored.

It is a further advantage of the invention that changes perceived in the activities of the monitored person, the companion and pet can be used for deducing that an event noticed by the companion or pet, such as a sudden illness or injury, has occurred.

The method according to the invention for evaluating activity and functional ability of a person, where a first wireless monitoring device is used for measuring in real-time activity data of a living target being monitored, is characterised in that the method comprises measuring with a second wireless monitoring device in real-time activity data of a second living target
  selecting at least one evaluation parameter illustrating interaction between the first living target and the second living target, which evaluation parameter is used in evaluating activity and functional ability and is included in the activity data
  comparing short-term measuring data illustrating interaction between both the first living target and the second living target to long-term corresponding measuring data of the evaluation parameters and
  sending based on the comparison information about a change in the activity and functional ability of the first living target to at least one data processing device, if a threshold value set for the evaluation parameter illustrating the interaction is not fulfilled.

The arrangement according to the invention for monitoring activity and functional ability of a living target, where a first wireless monitoring device is used for measuring in real-time activity data of a living target being monitored, is characterised in that the monitoring arrangement comprises a second wireless monitoring device, which comprises means for determining a change in location, activity and physiological state of a second living target in real-time and means for establishing a data transfer connection to a wireless data transfer network
  means for storing location data, activity data and physiological state data of the second living target in a database accessible via the data transfer network
  means for selecting at least one evaluation parameter illustrating interaction between the first living target and the second living target, which evaluation parameter is used in the evaluation of the activity and functional ability of the first living target
  means for comparing short-term measuring data of evaluation parameters illustrating interaction between both the first living target and the second living target to corresponding long-term measuring data and
  means for sending information describing a change perceived based on the comparison in the activity and functional ability of the first living target to at least one data processing device, if a threshold value set for the evaluation parameter illustrating the interaction is not fulfilled.

The server according to the invention utilised in the arrangement for monitoring activity and functional ability of a living target is characterised in that it comprises means for receiving activity data sent from the monitoring device of a second living target, which activity data comprises real-time location data of the second living target and at least one piece of data describing the activity of the second living target
  means for selecting at least one evaluation parameter illustrating interaction between the first living target and the second living target, which evaluation parameter is used in the evaluation of the activity and functional ability of the first living target
  means for comparing short-term measuring data of evaluation parameters illustrating interaction between both the first living target and the second living target to corresponding long-term measuring data and
  means for sending information describing a change perceived based on the comparison in the activity and functional ability of the first living target to at least one data processing device, if a threshold value set for the evaluation parameter illustrating the interaction is not fulfilled.

The computer program product according to the invention, which is utilised in evaluating the functional ability and activity of a person, is characterised in that it comprises computer code means stored in a computer readable storage means, which code means are configured to select at least one evaluation parameter illustrating interaction between a first living target and a second living target, which evaluation parameter is used in evaluating activity and functional ability and is included in the activity data
  compare short-term measuring data of an evaluation parameter illustrating interaction between both the first living target and the second living target to long-term corresponding measuring data of the evaluation parameters and
  send based on the comparison information about a change in the activity and functional ability of the first living target to at least one data processing device, if a threshold value set for the evaluation parameter illustrating the interaction is not fulfilled.

Some advantageous embodiments of the invention are presented in the dependent claims.

The basic idea of the invention is the following: The living target to be monitored, such as a human, a companion, such as a living companion or a possible pet, is equipped with a device, which is able to convey different data illustrating physiological measuring results, state and movement of the person and/or pet via radio contact to a data processing device in the home. The device carried by the person, companion and/or pet advantageously comprises a processor unit and a thereto connected memory unit, a transmitter-receiver, at least one 3D motion measuring sensor and a microphone. The motion measuring sensor may comprise 3D acceleration, compass and gyro sensors or some of these. The device carried by the person and/or pet may also comprise a sound or ultrasound echo sounder, a loudspeaker, an RFID tag or reader, a thermometer and measuring sensors monitoring the vital functions of the person, living companion or other companion or pet.

When the person, companion and/or pet moves, the 3D motion measuring sensor is used to calculate the person's, companion's and/or pet's location after a set time interval. Each location data is first stored in the memory unit of the device carried by the monitored person, companion and/or pet. At times the location data is sent to a PC in the home. The location data can also be sent to the PC continuously in real-time. Measuring data from the sensors can also be sent to the PC, whereby calculation of the location data occurs only with the PC. For example a transmitter-receiver connected to a USB port (Universal Serial Bus) of a PC can function as a base station.

All the other measuring data describing the behaviour or the physical state of the person, companion and/or pet are also transferred to a PC in the home. Examples of such data are the sleeping, eating and recreational location of the person and companion or pet and time spent in these locations and different vital function measuring results. Resting place and resting time, sounds, body temperature, heart rate and eating and drinking occurrences of the person, companion and/or pet are also transferred to the above-mentioned PC.

From the PC in the home the obtained measuring data is advantageously transferred to a server on the internet. Via the server, information describing the functional ability of the monitored person, companion and/or pet can be offered to an outside person, i.e. a person performing the monitoring, who has permission and/or a duty to monitor the functional ability and changes therein of the monitored person. With the aid of the data comprised in the server an outside person can be presented with behaviour and state data of the monitored person, companion and/or pet for a time interval determined by the outside person. By utilising the long-term monitoring results included in the server, interactive changes occurring in the behaviour of the monitored person, companion and/or pet may be discovered, which changes are not discovered solely from the real-time monitoring data of one target. Such a monitoring gives a picture of discrepancies occurring in the functional ability and interaction of the monitored person, companion and/or pet. When an application operating in the server notices a deviating feature in the physiological measurements or interaction of the person, companion and/or pet, it sends an alarm to the person performing the monitoring or another predetermined outside person or party.

BRIEF DESCRIPTION OF THE DRAWINGS

In the following, the invention will be described in detail. In the description, reference is made to the enclosed drawings, in which.

DETAILED DESCRIPTION OF THE DRAWINGS

The embodiments in the following description are given as examples only and someone skilled in the art can carry out the basic idea of the invention also in some other way than what is described in the description. Though the description may refer to a certain embodiment or embodiments in several places, this does not mean that the reference would be directed towards only one described embodiment or that the described characteristic would be usable only in one described embodiment. The individual characteristics of two or more embodiments may be combined and new embodiments of the invention may thus be provided.

Figure 1:
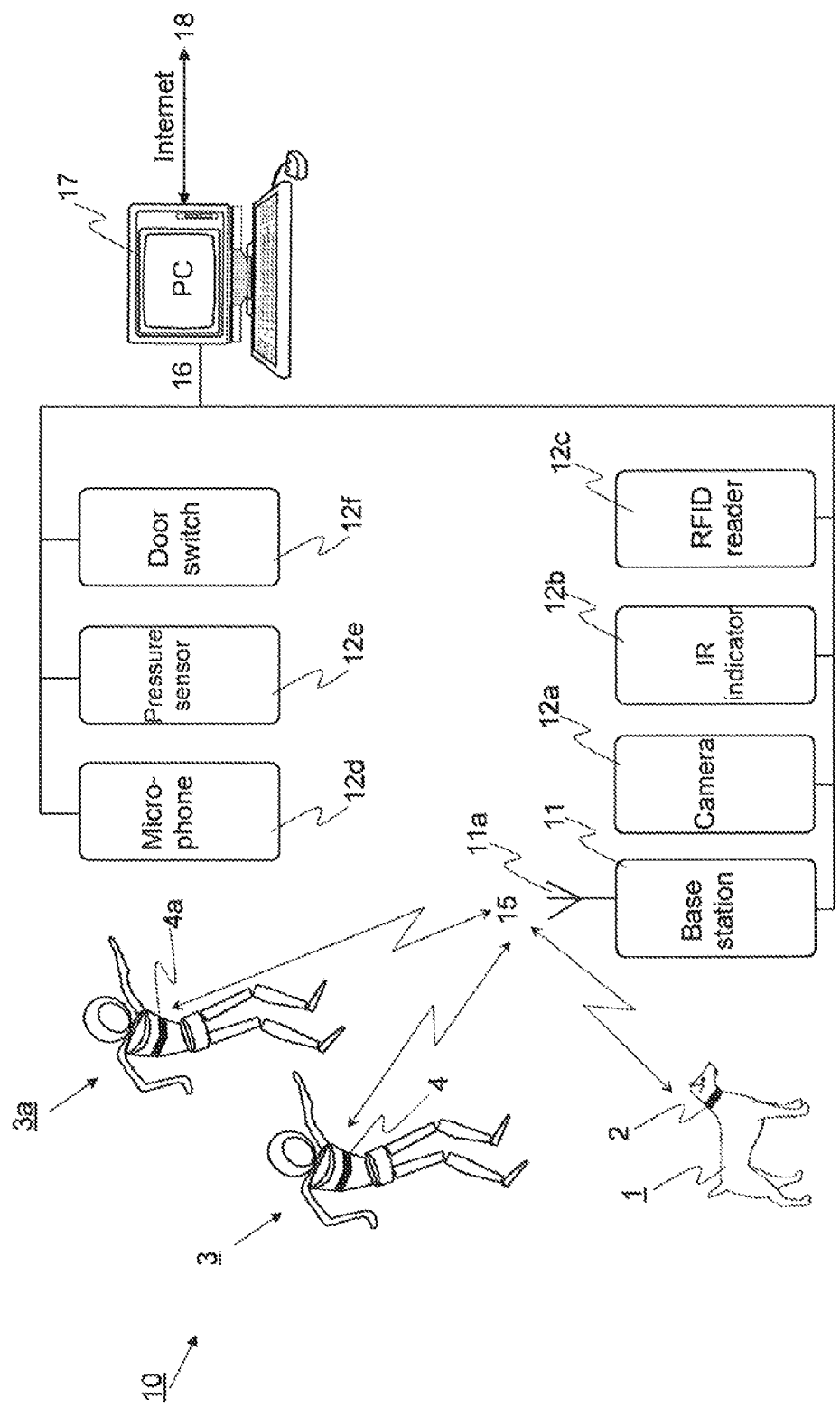
FIG. 1 shows a device arrangement according to an embodiment of the invention for monitoring activity and functional ability of a person.

FIG. 1 shows an example of an arrangement 10 for monitoring a living target, such as a human/person 3, a human companion 3a and/or a pet 1. Hereafter the word companion can mean either a human companion or the monitored person's pet. The actual monitored target is hereafter also called the first living target. The first living target may be either a human 3 or a pet 1. The companion of the monitored target is hereafter also called the second living target. The second living target may also be either a human 3a or a pet 1.

Figure 4A:
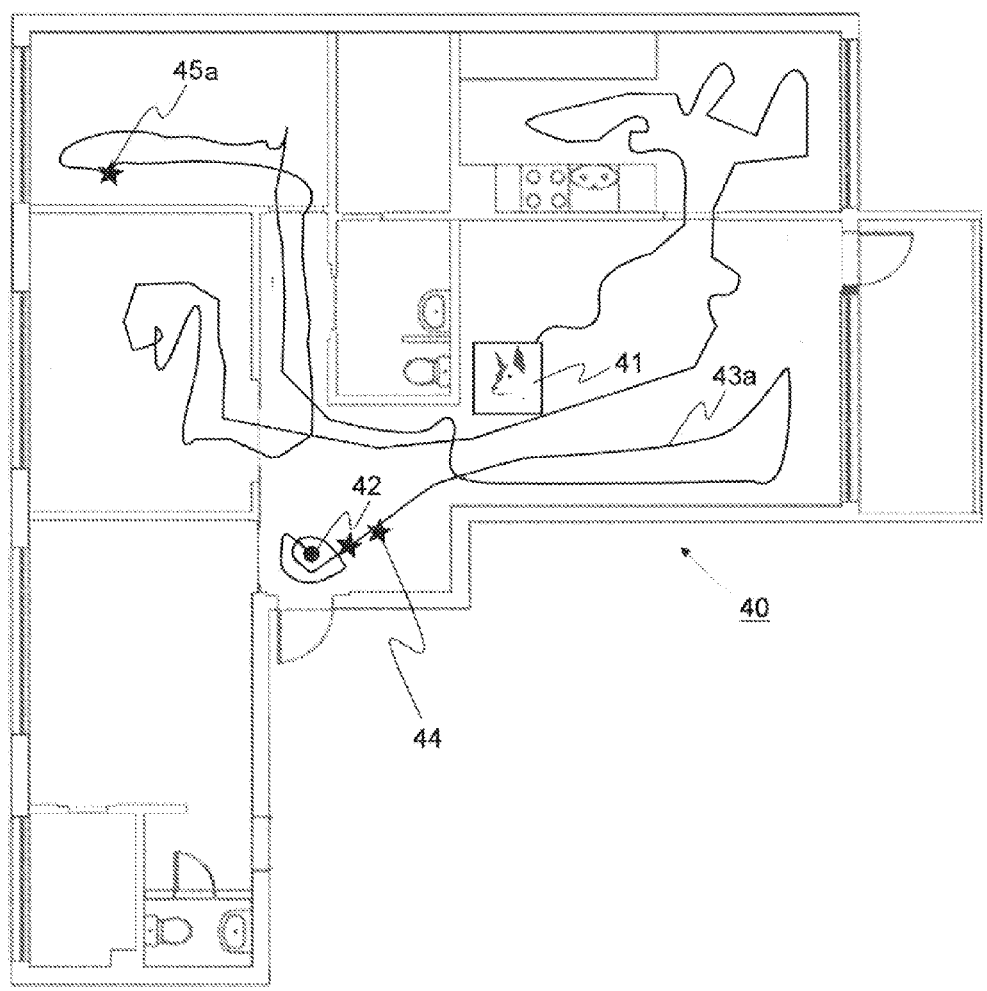
FIG. 4a shows an example of the presentation of the monitoring data of a pet on a monitoring person's device.
Figure 4B:
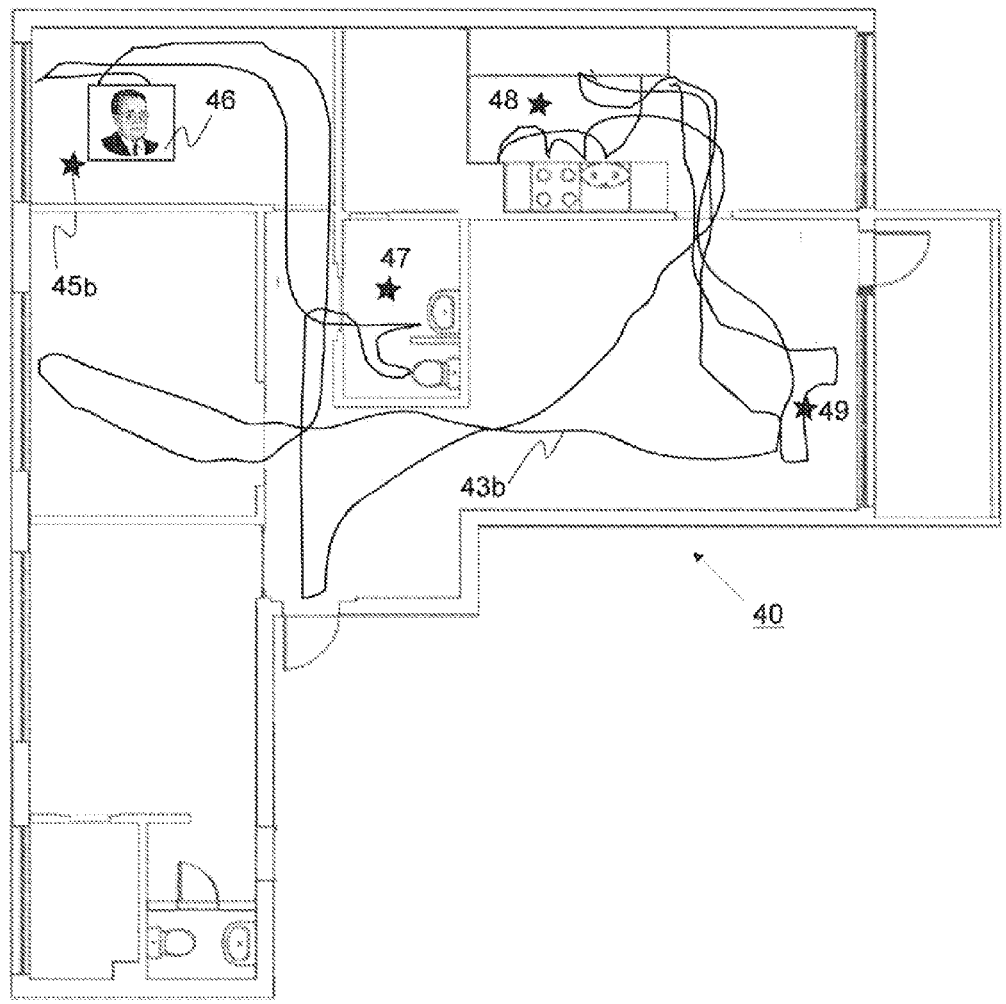
FIG. 4b shows an example of the presentation of the monitoring data of a monitored person on a monitoring person's device.
Figure 4C:
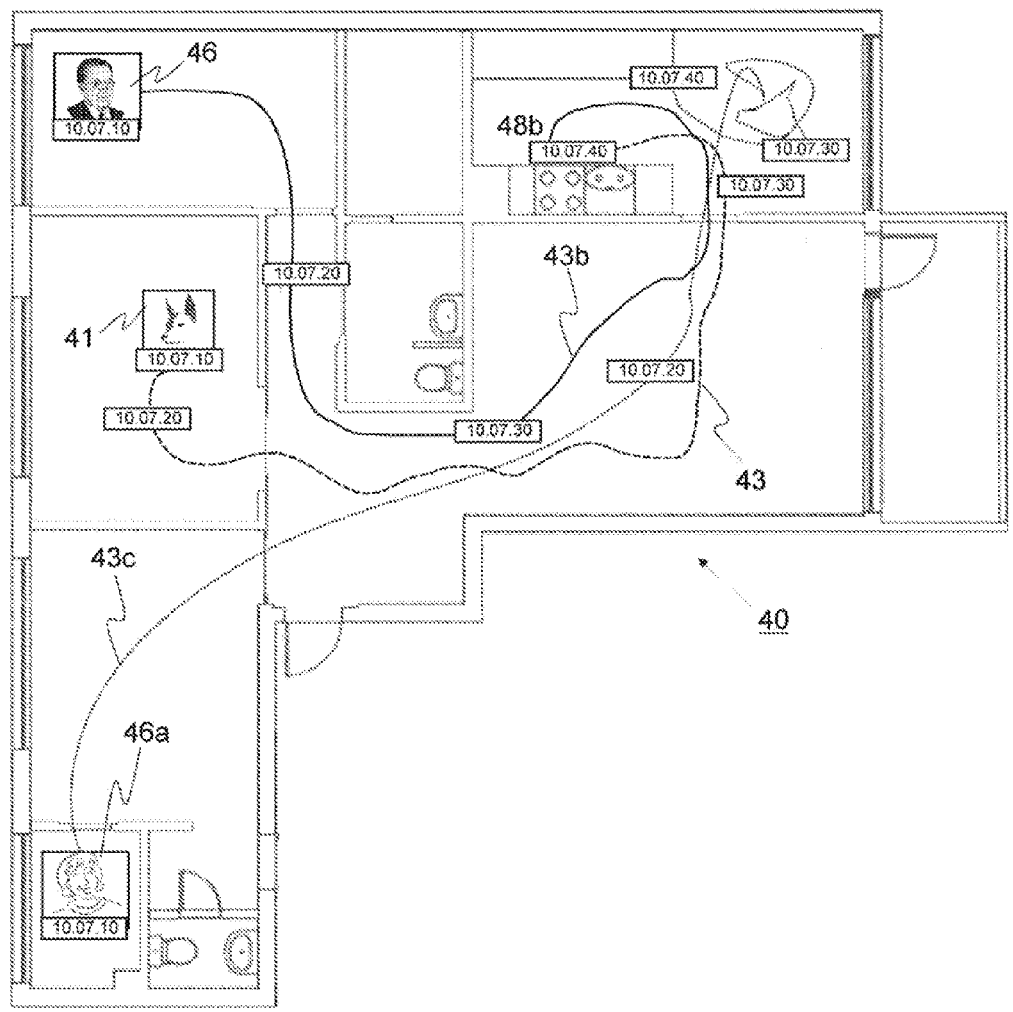
FIG. 4c shows an example of the movement of a monitored person, companion and/or pet over a certain time interval.

The monitoring arrangement 10 can be installed for example in an apartment which the monitored target uses as his apartment. An example of an apartment 40 is shown in FIGS. 4a, 4b and 4c. The exemplary arrangement 10 for monitoring a person shown in FIG. 1 advantageously comprises a wireless monitoring device 4 carried by the monitored person 3, a wireless monitoring device 4a carried by the companion 3a, a wireless monitoring device 2 carried by a possible pet 1, a base station 11 of a wireless data transfer network with an antenna 11a, a wireless data transfer network 15 and a computer 17. The monitoring environment 10 may advantageously also comprise one or several RFID readers (Radio Frequency IDentification) 12c, IR indicators 12b, video cameras 12a, microphones 12d, pressure sensors 12e and door switches 12f.

The monitoring devices 2, 4 and 4a according to the invention shown in FIG. 1 are connected via a wireless radio link 15 to at least one base station 11 belonging to the monitoring arrangement 10. The base station 11 can for example be a device, which can be connected to a USB port in a computer. The wireless radio link 15 can for example be an infrared link (IR), a Bluetooth link, a ZigBee link, a UWB link (Ultra WideBand), a WLAN link (Wireless Local Area Network) or some cellular network link. Because the distance between the monitoring devices 2, 4, 4a and the base station 11 of the wireless radio network is small, the transmission powers of the monitoring devices 2, 4 and 4a are also small. This makes possible a long operating time for the monitoring devices 2, 4 and 4a.

With the aid of the monitoring arrangement 10 according to the invention one can provide "remote care" or "remote monitoring" of a monitored person 3 and/or the person's pet 1. Via the arrangement the monitoring of the vital functions of a monitored person 3 and/or pet 1 can be monitored in various interactive situations either with each other or with a companion 3a. The invention makes possible the monitoring of a monitored person's 3 activity and functional ability by means of measurements of the vital functions of the person 3, companion 3a and pet 1 and by monitoring and analysing interaction between different parties. In the arrangement according to the invention a relative or friend does not have to physically go to monitored person 3 or pet 1.

The monitored person 3 and companion 3a shown in the example of FIG. 1 may be spouses and the possible monitored pet 1 may for example be a dog. The monitoring system according to the invention is especially well suited for situations, where the spouse in worse shape is the monitored person 3 and the one in better shape is the companion 3a. In the shown exemplary monitoring system 10 the person 3, the companion 3a and the pet 1 are equipped with at least one monitoring device 2, 4 and 4a according to the invention. If the pet 1 is a dog, the monitoring device 2 can advantageously be shaped as a collar, which the dog carries at all times.

All the monitoring devices 2, 4 and 4a shown in FIG. 1 advantageously comprise a 3D motion sensor, which advantageously comprises a 3D acceleration sensor, a 3D gyro sensor and a 3D magnetometer sensor. By integrating the measuring data from the motion sensor over time one can discover the movements of the monitored person, companion and pet, with the magnetometer the direction of the movement and with the gyro sensor even quick changes in the movement directions, whereby by combining these one can calculate the travel path of each of the above-mentioned targets in the apartment during the selected time interval.

The data from the 3D motion sensor can advantageously also be used for drawing a "map" of the apartment with the aid of the monitoring device 2, 4 or 4a registering the movement of the monitored person 3 or pet 1 so that the companion or pet owner moves the 3D acceleration sensor included in the monitoring device all over the apartment.

The floor plan of the room can be obtained for example as follows. The monitoring device 2, 4 or 4a is taken in the apartment to a set "home location". In the home location the motion measurement is started in the monitoring device 2, 4 or 4a. Thereafter one moves with the monitoring device in hand from the home place to the closest room corner by turning for example clockwise. The monitoring device is held in a substantially horizontal position near the corner (for example about 10 cm from both walls, or if it is an outer corner about 10 cm from the corner). At the corner the location measurement is registered again for example by pressing a button in the monitoring device. Thereafter one keeps moving in a clockwise direction to the next corner and acting in the above described manner. In order to obtain a floor plan of the apartment, the entire apartment is circled by following the walls. Each time when turning in a new direction in a slanting or straight angle, the location measurement is registered.

When finally arriving back at the starting point, i.e. at the home location, the monitoring device 2, 4 or 4a is deactivated with a suitable function related to the monitoring device 2, 4 and 4a.

Thereafter the monitoring device 2, 4 or 4a is connected to a computer and the therein generated floor plan is accepted. If needed, the image can be edited, for example windows and furniture can be added and the locations of walls and corners can be moved.

The 3D acceleration sensor is an example of a motion sensor, with which the location of a monitored target, such as a person, a companion or a pet, can be determined three-dimensionally. Other locationing technologies can also be utilised in the monitoring system according to the invention. The monitoring device 2, 4 or 4a can also contain a compass or a gyro sensor, which can be utilised in determining the movement directions. Examples of other positioning technologies are the RSSI (received signal strength indication) and TOF method (time of flight) known from wireless sensor networks applied to radio waves or ultra sound and locationing based on RFID readers. The location data calculated by the 3D acceleration sensor can advantageously be calibrated and specified from time to time for example by means of fixed RFID readers 12c or IR indicators 12b.

The location data of the monitored person 3, the companion 3a and/or the pet 1 can advantageously be calibrated for example with the aid of the sleeping/resting place. The sleeping place and sleeping position are often unchanged from day to day. The person, companion and/or pet sleeping or resting is indicated by the fact that no new acceleration data is received during a certain time. When the person 3, companion 3a or pet 1 finally begins to move, the defined sleeping place data and the acceleration measuring data can be used to determine a probable movement direction. If, when starting to move, the person or pet seems to be walking "through a wall", the monitoring system knows that the co-ordinates of the monitoring device 2, 4 or 4a have turned during the sleep or rest. In that case the monitoring system turns or moves the co-ordinates of the floor plan of the apartment so that the perceived path can be fitted into the floor plan of the apartment. Further in such cases, other locationing methods can also be used when the person or pet moves, in order for the location to be determined precisely at a certain time. When the precise locationing has been done once, the acceleration measurement can again be utilised alone to monitor the movement. Such a monitoring system does not necessarily need measuring of the compass direction at any time.

In the monitoring system according to the invention the movement of the monitored person 3, the companion 3a and/or the pet 1 is monitored and stored continuously. This makes it possible that the movement of the person 3, companion 3a and/or pet 1 in the apartment can advantageously be stored over a longer time period. The stored data can be processed statistically and/or by utilising a neural network. Data describing the movement and interaction between the person, companion and/or pet processed in this manner can be utilised for sending possible alarms. For example unusually active movement and/or sounds of the companion 3a and/or pet 1 in a situation, where the monitored person 3 remains in place, indicates that the functional ability of the monitored person 3 has for some reason or another significantly weakened. An unusual physiological measuring result in a certain interactive situation may also give an indication of a change in the functional ability of the monitored person 3.

The movement time of the monitored person 3, companion 3a and/or pet 1 can advantageously be coded with different colours or line shapes or it can at applicable time intervals be added to a drawn travel path pattern. For example bright red can illustrate the activity history of the last 15 minutes, yellow the history from 15-60 minutes ago, green the history from 1-3 hours ago, etc.

The monitoring system 10 advantageously comprises means with which the travel path of the person 3, companion 3a and/or pet 1 can be analysed by calculating a correlation for example with the paths of the previous days. The latest travel path of the monitored person 3, companion 3a and/or pet 1 can for example be compared to an average path of the travel paths of the ten previous days at a certain time of the day. Data used in the comparison can be for example how many minutes the monitored person 3, companion 3a and/or pet 1 on average stays at the sleeping place, the front door, in the kitchen, at the resting place of the monitored person 3 etc. By combining also physiological data obtained from the measurements of vital functions to these activity data, a clear picture of the functional state of the monitored person is obtained.

Alternatively a neural network can be used for interpreting the travel paths, vital function measuring data and interactive situations.

A SOM neural network (Self-Organising Map) is one neural network, which can be utilised in the invention. In the SOM neural network statistical connections between the multi-dimensional entered data cluster elements are converted into simple geometrical ratios.

The SOM neural network is updated with the following algorithm (1):

$$\|x(t_k)-m_i(t_k)\|=\min_i\{\|x(t_k)-m_i(t_k)\|\}, \quad (1)$$

where $x(t_k)$ is a multi-dimensional data vector received by the SOM neural network and $m_i(t_k)$ is an artificial neuron, i.e. a weight vector. Time is expressed with the variable $t_k$.

Equations (2) and (3) can be used as an updating rule for the weight vector:

$$m_i(t_{k+1})=m_i(t_k)+\alpha(t_k)[x(t_k)-m_i(t_k)], i\in N_c \quad (2)$$

$$m_i(t_{k+1})=m_i(t_k), \text{otherwise}. \quad (3)$$

Parameter $\alpha$ is a "forgetting term", on the size of which it depends, how much of the old neuron value is left in the updating. It also controls the network stability. $N_c$ is a topological neighbourhood, i.e. a set of neurons, which in the network are closest to the neuron implementing the minimum operation.

The updating adjustment of the map means that the neurons $m_i$ closest to the data vector x are moved toward the data vector x. Thus the neurons of the SOM neural network learn/are tuned through the input variables they receive.

In the monitoring system according to the invention the SOM neural network learns or is taught to know the monitored person's 3 interactive events and reactions associated with them with the companion 3a and/or pet 1 at different times of the day. At the same time physiological measuring data obtained from measuring vital functions are registered and they are combined with this interactive event. If the detected interactive event does not correspond to an interactive event known by the SOM neural network and physiological measuring results describing vital functions associated therewith, then in this case an alarm message is sent to a party performing the monitoring.

The neural network can advantageously be taught to give an alarm when one or a certain combination of thresholds given for the evaluation parameters are exceeded, undercut or their combination is an undesired combination. By using the neural network an alarm can be provided for example when a certain combination of travel paths (or measuring data) of the person, companion and/or pet occurs in a way which deviates from the normal situation. For example some interactive event between the person, companion and/or pet has changed to be more active than usual. Anomalous data obtained from the measuring of vital functions combined with a certain known interactive event also causes an alarm.

The monitoring arrangement according to the invention can be used for examining in what part of the apartment the person 3, companion 3a and/or possible pet 1 have moved, where and at what time of the day interaction has been detected and for how long the interactive event has lasted. What kind of physiological measuring data has been measured from the interactive event in question is also discovered.

A computer program in a computer 17 can also give an alarm based on movement or sounds of the person 3, companion 3a and/or pet 1 which differ from what is normal or based on some anomalous measuring result measured from the monitored target. If the companion 3a or pet 1 for example stays longer than a certain amount of time by the person's 3 resting place and if the pet for example barks more than a preset barking limit, an SMS alarm can advantageously be sent to a relative or friend performing the monitoring or a Skype call can directly be opened, by means of which one can listen to and/or see what is happening in the apartment. Similarly if the companion's 3a heart rate, breathing frequency or sound level and pitch surprisingly change near the monitored person 3, the monitoring system advantageously sends and alarm. Such a situation may for example mean that the companion 3a has found the monitored person 3 who has had a sudden illness, but cannot immediately act in a manner required by the situation.

In one embodiment of the invention the person 3, companion 3a and/or pet 1 are equipped with several different monitoring devices. For example a 3D monitoring device 2 for a dog monitors the dog's movement and a second monitoring device (not shown in FIG. 1), which is connected to the actual monitoring device 2 either via a wired or wireless connection, makes it possible to monitor for example how the dog whips its tail and/or its vital functions, such as body temperature and heart rate.

For the person 3 or companion 3a there may be for example six different measuring sensors. The actual monitoring device 4 can advantageously be attached at chest height for example as a belt reaching around the body. The actual monitoring device 4, 4a manages the data transfer to the closest base station 11 belonging to the system. Some examples of placements for other sensors are a band on the head or glasses and sensors on the wrists and ankles.

A band around the head can advantageously indicate for example head movement, eye and ear movement or it can even measure brain wave functions.

Figure 2:
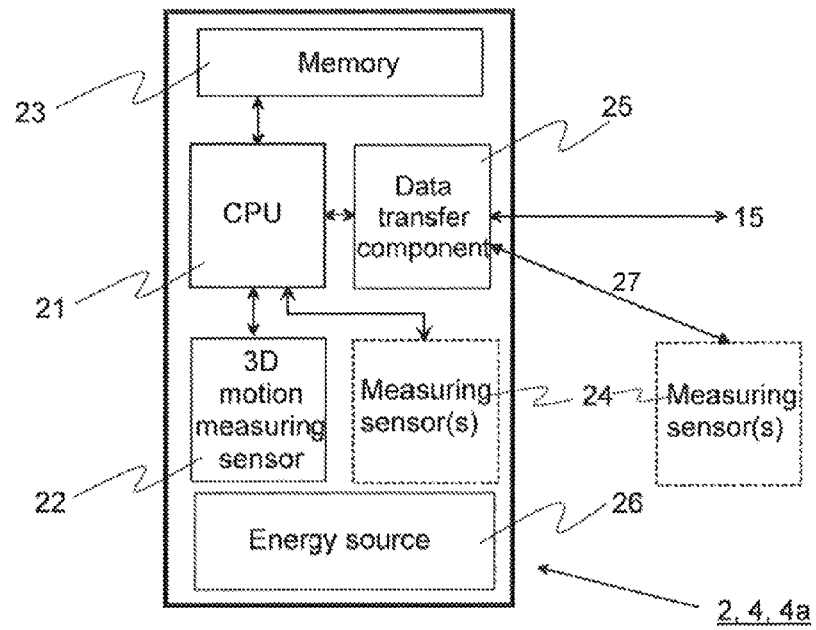
FIG. 2 shows an advantageous embodiment of a monitoring device carried by a monitored person, companion and/or pet.

FIG. 2 shows an advantageous embodiment of a monitoring device 4, 4a or 2 carried by the person 3, companion 3a and/or pet 1. In the following description the monitoring device is often referred to only with reference number 2. The monitoring device 2 advantageously comprises an energy source 26, such as a battery or an accumulator. The energy source 26 can advantageously be charged for example by connecting it to a USB port in a computer. The electric components in the monitoring device 2 get the energy they need for their function from this energy source 26. There is at least one 3D motion sensor 22 in the monitoring device 2. The measuring area of the 3D acceleration sensor used therein is advantageously ±10 g.

The measuring data from the 3D motion sensor 22 is processed in the measuring event in the processing unit 21 (CPU, Central Processing Unit) of the monitoring device 2. The processing unit 21 is connected to a memory 23. The memory 23 is used for storing the computer programs needed in the processing of measuring values according to the invention. All the variable values measured with the monitoring device 2 are also stored at least temporarily in the memory 23. Results calculated in the monitoring device 2 from the measured variables are also stored in the memory 23.

An example of the calculation of a variable performed by the processing unit 21 is the calculation of the location data using measured acceleration data. The location calculation program according to the invention is stored in the memory 23. The computer program comprises computer program commands, by using which the processing unit 21 calculates from the 3D acceleration measuring data the displacement of the monitoring device 2 in three dimensions between two consecutive acceleration measurements.

The processing unit 21 is also connected to a data transfer component 25. With the aid of this data transfer component a data transfer connection 15 is established to a base station 11 of a wireless data transfer network belonging to the monitoring system. The data transfer component 25 advantageously supports at least one data transfer method. Some advantageous methods usable in data transfer are infrared technology (IR), Bluetooth technology, ZigBee technology, UWB technology, WLAN technology and various time or code division data transfer technologies used in cellular networks. Measuring data stored in the memory 23 of the monitoring device 2 via the data transfer component are transferred via the wireless data transfer connection 15 to the base station 11. From the base station the measuring data is transferred via the data transfer connection 16 to the computer 17 to be stored. The data transfer connection 16 can be either a wireless connection or a cable connection or a combination thereof.

The data transfer component 25 advantageously also comprises data transfer means, which can communicate with a RFID reader. By using data from the RFID reader 12c, the location data of the monitoring device 2 calculated from the data of the 3D acceleration sensor can be confirmed in the computer 17 for example in a situation, where the person 3 or pet 1 seems to be passing "through a wall". When needed, the location data calculated from the acceleration measuring data is advantageously corrected to correspond to the location data received from the RFID reader 12c.

The monitoring device 2 can advantageously comprise also other measuring sensors 24 than the 3D acceleration sensor 22. The other sensors can be either a part of the monitoring device 2, 4 or 4a or they may be separate sensors on different parts of the person's or pet's body. The measuring data from these sensors is transferred to the monitoring device 2 either via a wired or wireless data transfer connection 27.

Examples of other types of sensors are a compass, a gyro sensor and an air pressure sensor, with which a relative change in height can be measured. Sensors measuring physiological properties can also be included in the monitoring device 2 according to the invention. Examples of such sensors are a sensor measuring body temperature, a sensor measuring breathing functions, a sensor measuring muscle movements, a sensor measuring head movements, a sensor monitoring heart rate, a sensor monitoring brain functions, a sound or speech sensor and a barking sensor. The processing unit 21 processes the data also from these measuring sensors and stores it at least temporarily in the memory 23. In connection with the storing the processing unit 21 combines the data from other measuring sensors with the location data received from the acceleration sensor 22. The combined measuring data is stored in the memory 23, from where it is transferred at times to the computer 17 for further processing.

When a person 3, companion 3a and/or pet 1 starts to move after lying down, it is possible that the coordinates of the monitoring device 2, 4 or 4a have rotated while the person, companion or pet was resting. Due to the rotation of the coordinates it may seem like the person, companion or pet is moving "through a wall". In such a case the measuring data from a compass or a gyro sensor can in an embodiment of the invention be utilised in determining the movement direction of the person, companion or pet when the targets start to move after lying down. From this measuring data the real direction the monitored target starts to move in can be discovered, with which direction the direction data given by the acceleration measurement is advantageously corrected.

In a second embodiment of the invention the known resting/home place and sleeping position of the person 3, companion 3a and/or pet 1 can be utilised also for calibrating the coordinates of the monitoring device 2, 4 and 4a. If the person 3, companion 3a and pet mostly sleeps in the same position/direction, the monitoring system advantageously updates/calibrates the co-ordinates of the sleeping place from this still staying data.

In an advantageous embodiment of the invention the monitoring system learns to make standard corrections automatically after it has done the same "walking through a wall" correction already a few times and noticed that the "walking through walls" stops with said corrections of the coordinates.

The movement of the target or targets from one place to another can be monitored with the aid of the measuring data obtained from the monitoring device 2, 4 or 4a. The data can also be used for deducing the manner of movement, such as walking, running or crawling. The measuring data can be used for deducing also the monitored target's position, such as standing, sitting, laying or some anomalous position. Sensors attached to the wrists and ankles can also be used for measuring movements of the limbs and possible tremors in them.

The monitoring device 2, 4 or 4a can also be used to monitor the sound-making manner of the target, such as sound volume, sound pitch, duration of sound making, repetition of sound making and unusual sounds. For example speech, yelling, crying, yawning, breathing sounds and moaning can advantageously be separated from the sounds of a human. For example barking, meowing, growling, purring, neighing, movement sounds, breathing sounds, yawning and whining can advantageously be separated from the sounds of a pet.

By combining all the above-described measuring data a picture is obtained of an interactive event between a person 3 and a companion 3a and/or pet 1 and of the state of their vital functions at the moment. When the system has been taught the interactive events associated with normal life and physiological measuring results describing vital functions related thereto, then the system separates vital function levels deviating from the normal in different interactive situations for example by statistical calculation methods or by utilising neural network technology.

Figure 3:
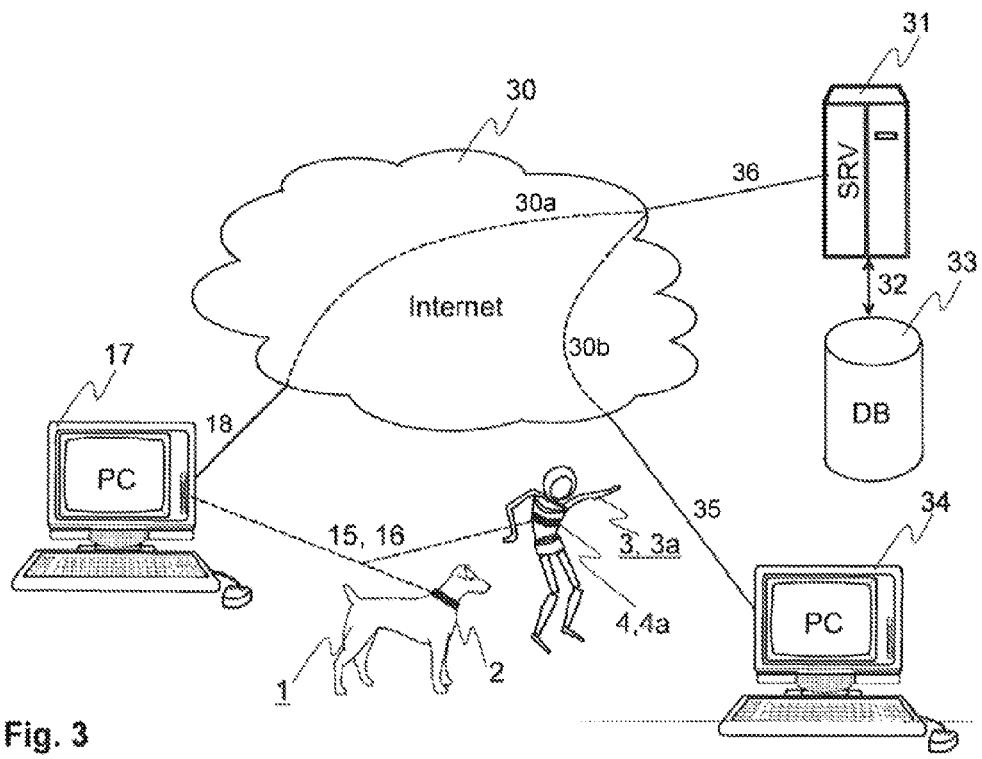
FIG. 3 shows an advantageous embodiment of a data transfer arrangement used in the monitoring of a monitored person, companion and/or pet.

FIG. 3 shows one example of utilising monitoring data in an internet environment. The pet 1 has a monitoring device 2, which continuously measures at least the whereabouts of the pet. The monitored person 3 has a monitoring device 4, which continuously measures the whereabouts of the monitored person. FIG. 3 does not separately show the companion 3a, who may for example be the monitored person's living companion, and his monitoring device 4a. The monitoring data of all targets is transferred via a data transfer network 16, 15 to a computer 17. The measuring data is stored in the computer 17 at least temporarily.

A data transfer connection 18 can be established from the computer 17 to the internet 30. The server 31, which is advantageously used for utilising the monitoring data, is also connected via a data transfer connection 36 to the internet. A data transfer connection 30a can thus be established via the internet between the computer 17 and the server 31. This arrangement makes possible the transfer of the measuring data received from the monitoring device 2, 4 and 4a from the computer 17 to the server 31 for further analysis and possible presentation. The transferred measuring data from the monitoring device is stored in a database 33 via the data transfer connection 32.

Reference number 34 shows a second data processing device, which is able to establish a data transfer connection 35 to the internet 30. Via the data transfer connection 30b established to the internet, an analysis and presentation request for data regarding the monitoring devices 2, 4 and/or 4a can be made from the data processing device 34 to the server 31. The server 31 checks if the service request made by the data processing device 34 is allowed or not. If the service request is allowed, the server 31 retrieves the data of the monitoring devices 2, 4 and/or 4a defined in the service request from the database 33 for the time period defined in the service request. The server 31 processes the measuring data and sends the processed data to the data processing device 34. The data processing device 34 may be a data processing device used by some relative or friend or a data processing device of some third party, who is allowed to monitor the functional ability of the person 3 or pet 1.

FIG. 4a shows an example of a pattern illustrating the movement of a dog presented in the monitoring system according to the invention. The floor plan of the apartment 40 is created with some graphic drawing program according to prior art. For example by moving the monitoring device 2 on the dog in the apartment 40, the dimensions of the floor plan can with the measuring sensor be calibrated into the measuring data of the monitoring device.

In the example in FIG. 4a the monitoring of the pet 1, for example dog, has started in point 41. The line 43a illustrates the movement of the dog in the apartment 40 during the time period selected as the monitoring period. The line 43a is advantageously modified in a way by which the movement of the dog at different times can be presented. The movement time can for example advantageously be coded with different colours or line shapes. For example bright red can illustrate the activity history of the last 15 minutes, yellow the history from 15-60 minutes ago, green the history from 1-3 hours ago, etc. By using coding procedures, a clear picture of the dog's movements at different times is obtained.

Reference number 42 illustrates the position of the latest measurement in this example. Reference number 44 can be used to illustrate for example the places, where the dog has for some reason or other barked or otherwise made sounds. Reference number 45a illustrates a place, where the dog has rested. If the measured rest place 45a is the usual place for the dog in question, the known rest place 45a can be used to calibrate the measuring data depicting the movement of the dog coming from the 3D acceleration sensor, when the dog starts to move after its rest. Thus a possible measurement error caused by turning of the measurement directions of the 3D sensor, which has happened during the rest, and inaccuracy of the acceleration measuring is avoided.

FIG. 4b shows an example of a pattern illustrating the movement of a person 46 presented in the monitoring system according to the invention in the same apartment, where the movement of a pet is shown in FIG. 4a.

In the example in FIG. 4b the monitoring of the person 46 has been started in point 45b. The line 43b illustrates the movement of the person 46 in the apartment 40 during the time period selected as the monitoring period. The line 43b is advantageously modified in a way by which the movement of the person at different times can be presented, as shown above.

Reference 47 shows the person using the restroom. Reference 48 shows the person's activity in the kitchen. Reference 49 shows a place where the person has rested or otherwise spent long times. The place 49 can for example be a sofa.

By combining the movement and interaction points of FIGS. 4a and 4b, an almost real-time picture of the person's 46 activities and functional state can be obtained. The server 31 belonging to the monitoring arrangement is able to deduce, by using the monitoring data, if the person's 46 functional ability has decreased so much that it absolutely requires that someone pays a visit.

FIG. 4c shows the mutual movement of a monitored person 46, a companion 46a and a dog 41 as a function of time in the apartment 40 shown in FIGS. 4a and 4b. In the travel graph of FIG. 4c one can advantageously mark the time at certain time intervals for the travel path 43, 43b and 43c of the monitored person 46, the companion 46a and the pet 41. In the example of the figure the person 46 has started moving from his room at the time 10.07.10. At the time 10.07.40 the person is in place 48b, which is situated in the kitchen. The travel path 43b is shown as a continuous line. Correspondingly the companion 46a has at the time 10.07.10 woken up to the movement of the person 46. The companion 46a is at the time 10.07.40 in the kitchen monitoring the activity of the person 46. Correspondingly the dog 41 has at the time 10.07.10 woken up to the movement of the person 46. The dog 41 is at the time 10.07.40 also in the kitchen monitoring the activity of the person 46.

In the example of FIG. 4c the movement of the companion 46a in the kitchen between the times 10.07.30 and 10.07.40 is chaotic. If at the same time the vital function measuring data of the companion 46a and the monitored person 46 also deviates from the normal, it is very likely question of a situation, where an alarm to an external party is needed. From the stored data corresponding movement series of the monitored person 46, the companion 46a and/or the pet 41 can advantageously be viewed as easily played animations.

When using neural network calculation, data regarding the current and previous (for example a 10 second history) location coordinates, movement directions and speeds, physiological measuring data of the person 46, companion 46a and/or pet 41 are entered as parameters into for example a SOM neural network, from which measuring data the neural network searches for commonalities and differences. By letting the neural network organise itself (learn) slowly for example during a month to recognise normal daily routines and physiological measuring results related thereto it becomes sensitive to abnormal interactive situations and can thus activate alarms.

Figure 5:
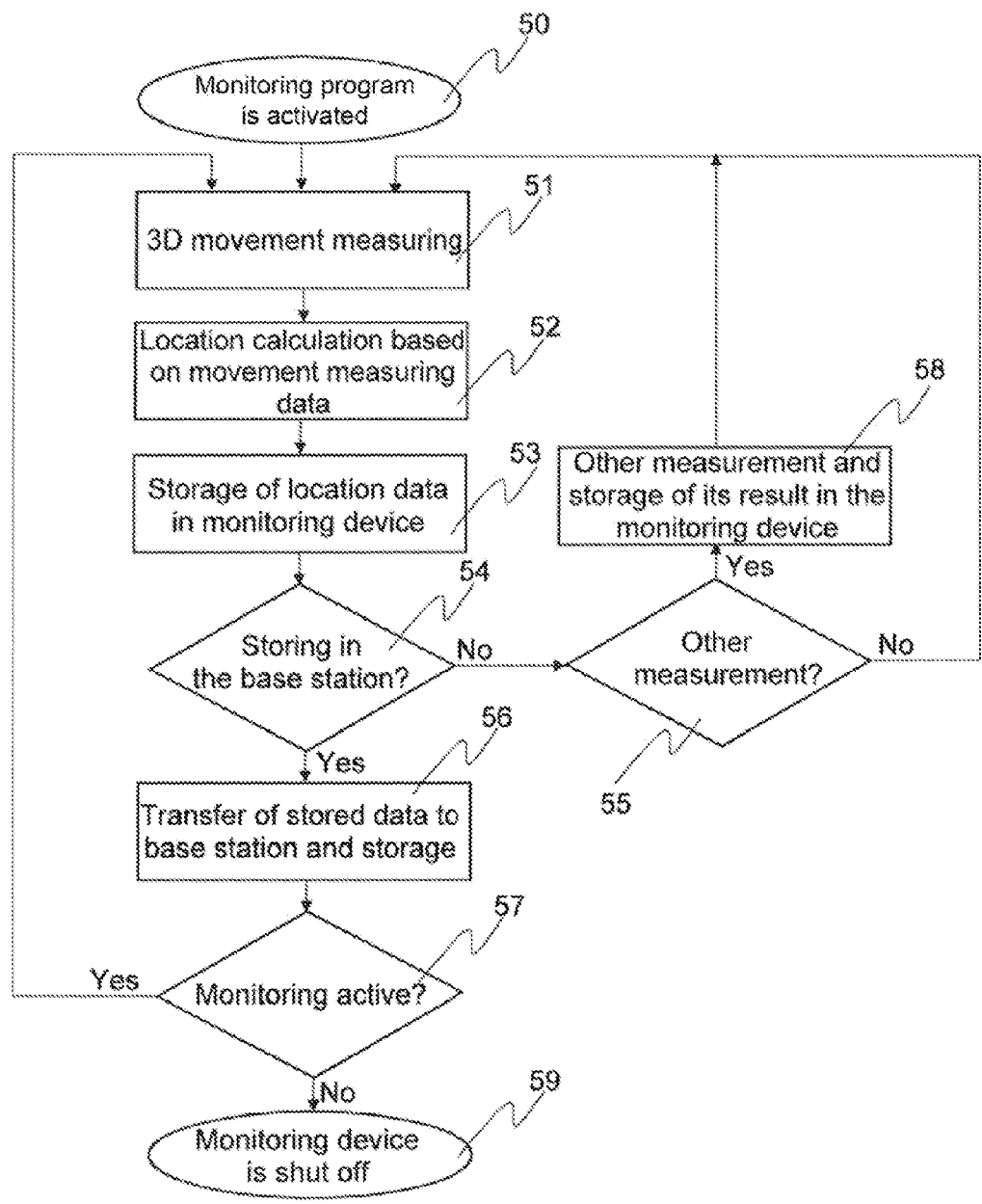
FIG. 5 shows as an exemplary flow chart the main functions performed by the device carried by the monitored person, companion and/or pet in the monitoring method according to the invention.

FIG. 5, by way of reference to FIGS. 1-3, shows as an exemplary flow chart the main functions performed by a monitoring device 2, 4 or 4a during monitoring. In the following description only reference number 2 is used when discussing the monitoring device, though the matter also concerns the monitoring device 4 or 4a. In step 50 the monitoring device 2 is activated. The monitoring device 2 can be activated for example by switching on power in the monitoring device 2 from a power switch in the monitoring device. As a result of the activation of the monitoring device 2 at least the 3D acceleration measurement starts 51 in the monitoring device. In connection with the activation the location of the monitoring device 2 in the used floor plan coordinates of the apartment is advantageously calibrated. Thereafter the monitoring device 2 continuously measures the accelerations in three mutually perpendicular dimensions.

In step 52 the processing unit 21 of the monitoring device 2 calculates, with two successive 3D motion measurements, how much and in which direction the monitoring device 2 has moved between these measurements. In step 53 the calculated location data is stored in the memory 23 of the monitoring device 2.

In step 54 a checking is performed to determine if the stored measuring data is transferred via the base station 11 to the computer 17. If it is in step 54 found that no storing is done at this time, the process moves to step 55, where a checking is performed to determine if some other measurement regarding the person 3, 3a or pet 1 should be performed. Such another measurement can be some measurement monitoring vital functions. If it is in step 55 found that no other measurements will be performed, the process returns to step 51, whereafter a new acceleration measurement is performed.

If it is in step 55 found that other measurements than the 3D motion measurement will be done, the process moves to step 58. In step 58 the other specified measurements are performed and their results are stored in the memory 23 of the monitoring device 2. Examples of such other possible measurements directed at the person 3 or 3a are heart rate, EKG, EEG and EMG curves, breathing sounds and blood oxygen saturation. The position of the target, such a for example standing, sitting or laying, can also be measured. The sound-making manner of the target, such as speech, yelling, crying, yawning, sound volume, sound pitch, length of sound, repetition of sound and moaning, are other possible measuring results.

Measuring data describing gestures and expressions of the person 3 or 3a and data describing limb movement can also be measured and stored.

In connection with the storing a temporal link is created between the measured other measuring data and the closest motion measuring data. By proceeding in this manner, the calculated location data and other measuring data describing interaction can be presented temporally in the correct time ratios later. After the storing the monitoring process returns to step 51, where a new 3D motion measurement is performed.

If it is in step 54 found that the measuring data stored in the memory 23 of the monitoring device 2 is transferred to the computer 17, the process branches out into step 56. The data transfer can be started for example at certain time intervals, when the storing capacity of the memory 23 is filled up or by a command coming from the computer 17. In step 56 the measuring data stored in the memory 23 of the monitoring device 2 is transferred via the base station 11 of the monitoring arrangement to the computer 17.

After the performed data transfer, a checking is performed in step 57 to determine if the monitoring is still in an active state or not. If the monitoring is still in the active state, the process returns to step 51, where a new 3D motion measurement is performed.

If it is in step 57 found that monitoring does not need to be done anymore, the monitoring device 2, 4 or 4a is switched off in step 59. The switching off can advantageously be done with a command sent by the computer 17 to the monitoring device 2, 4 or 4a. The received switch-off command is advantageously performed after the first data transfer step 56, which comes into turn to be performed after the switch-off command for the monitoring sent by the computer 17.

Figure 6:
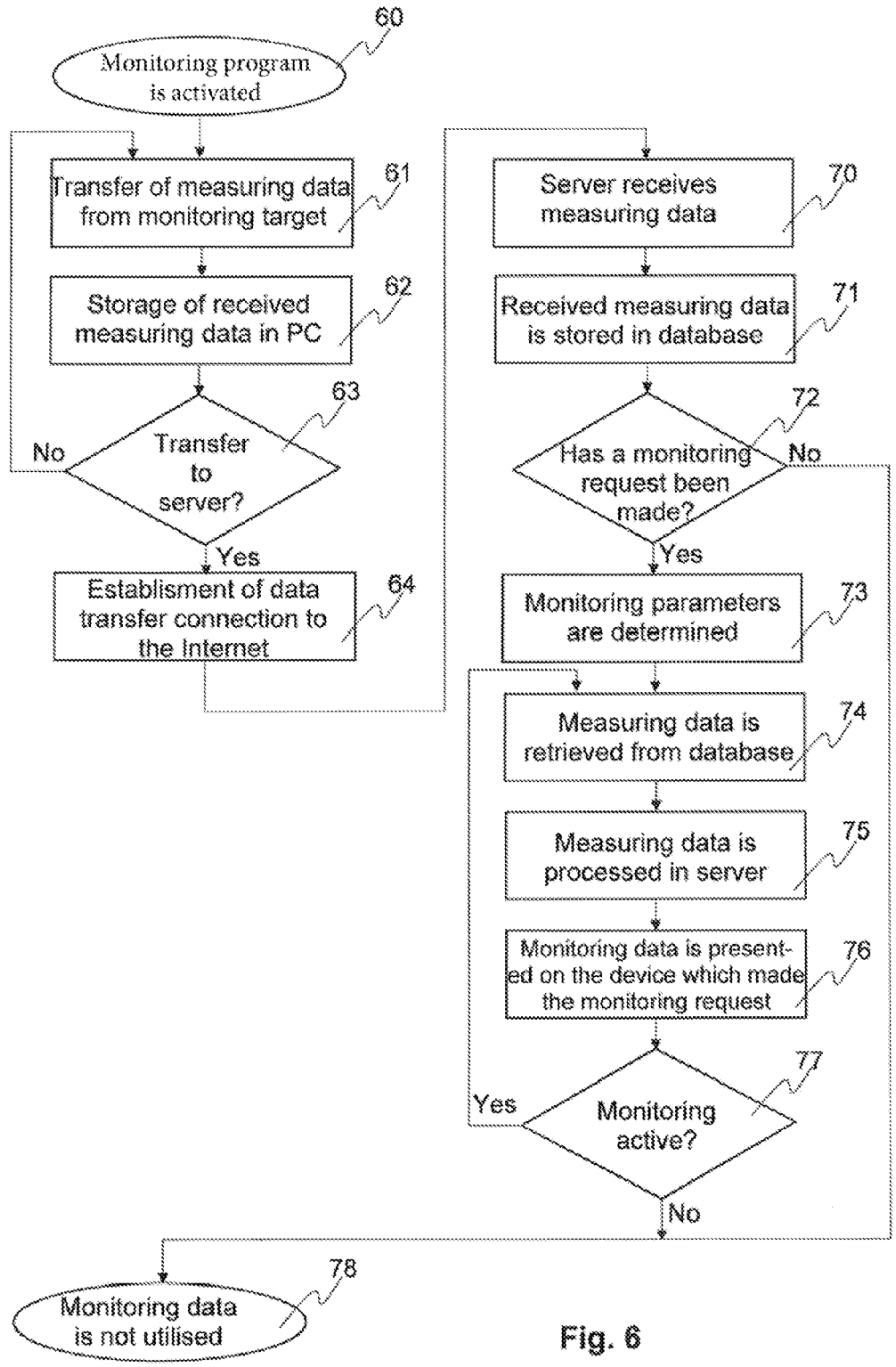
FIG. 6 shows as an exemplary flow chart the main steps used in presenting the monitoring data of a monitored person, companion and/or pet

FIG. 6 shows as an exemplary flow chart the main steps in the monitoring process of the computer 17 and server 31 during monitoring of a target. In step 60 the monitoring program in the computer 17 is activated. In the active state the computer 17 can receive and send information either from/to the server 31 or from/to the monitoring device 2, 4 or 4a.

In step 61 the measuring data in the memory 23 of the monitoring device 2, 4 or 4a is transferred to the computer 17. The data transfer can be started either by the computer 17 or the monitoring device.

In step 62 the measuring data received from the monitoring device 2, 4 or 4a is stored in the memory of the computer. When the received measuring data is stored, a checking is performed in step 63 to determine if the stored measuring data will be transferred to the server 31 or not. If the checking 63 gives the result that the measuring data is at this step not transferred to the server 31, the computer returns to step 61 to await the next transfer of measuring data from the monitoring device 2, 4 and 4a.

If the checking in step 63 gives the result that a transfer of measuring data to the server 31 should be performed, then in step 64 the computer 17 establishes a data transfer connection via the internet to the server 31.

In step 70 the computer 17 sends the measuring data stored last to the server 31, which receives the measuring data. In step 71 the server 31 stores the measuring data in a database 33. Thereafter a checking is advantageously performed in the server to determine if there is a monitoring request regarding the stored measuring data. If no monitoring request has been made, the server process moves to step 78, where the stored measuring data is not processed or presented to outside persons.

If it is in step 72 found that at least one monitoring request has been made regarding the monitoring devices 2, 4 and 4a, from which the measuring data was received, the process moves to step 73. In step 73 the evaluation parameters are checked or set. Examples of evaluation parameters are monitoring interval, location data and some physiological measuring result, such as for example body temperature or heart rate.

In step 74 the server retrieves the measuring data regarding the selected monitoring devices 2, 4 and 4a and the selected evaluation parameters from the database 33. In step 75 the server 31 processes the measuring data with a suitable computer program so that information regarding the selected parameters is discovered from the measuring data. If needed, a location and direction calibration is performed on the measuring data based on the last verified resting place before the measuring data is sent to the data processing device 34.

In step 76 the processed monitoring data is sent via the internet to the data processing device, which has made the accepted monitoring request. The processed monitoring data is transferred in ready presentation format to the data processing device 34, which made the monitoring request.

When the processing and presentation of the data has been made, a checking is next performed in step 77 to determine if some monitoring request regarding the monitoring devices 2, 4 and 4a is still in force. If there is no unanswered monitoring request, the process moves to step 78, where the measuring data in the database 33 is not at that moment utilised.

Figure 7:
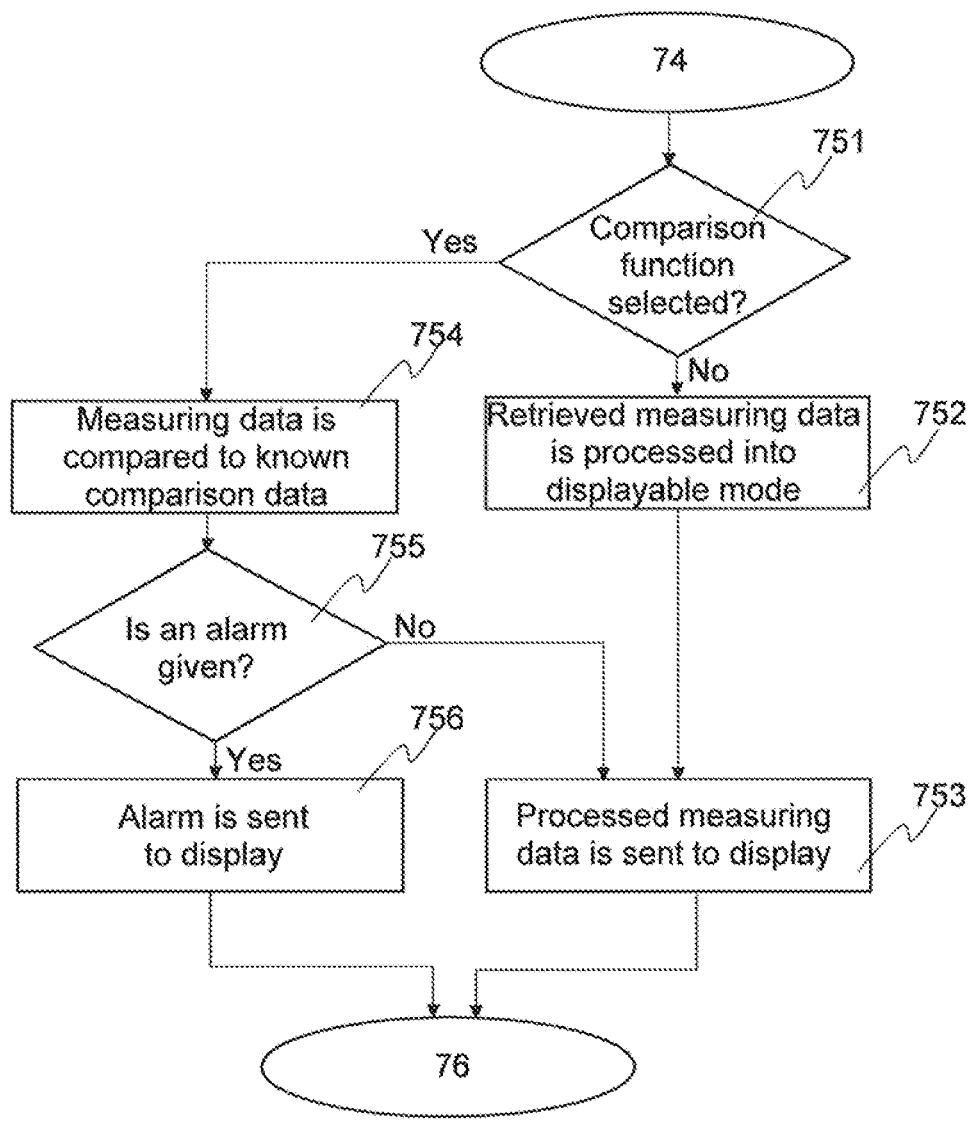
FIG. 7 shows as an exemplary flow chart how the monitoring data of a monitored person, companion and/or pet is used for giving an alarm.

FIG. 7 shows as an exemplary flow chart the programmatic main functions performed by the server in step 75 in FIG. 6 in a situation, where it is desired to compare the latest measuring data to long-term average data, for example in order to provide an alarm when the functional ability of the monitored target has weakened.

Step 751 consists of checking to see if a comparison of some evaluation parameter has been requested. As evaluation parameter can be selected for example monitoring of interactive events based on measuring data in the apartment or monitoring of physiological measuring data or a combination of them. If no comparison request has been made, then measuring data retrieved from the database 33 is in step 752 processed into a form suitable for the data processing device 34. In step 753 the processed data is sent to the data processing device 34 to be presented.

If it is in step 751 found that a comparison request for an evaluation parameter illustrating at least interaction and/or at least one evaluation parameter illustrating physiological measurements has been presented, the process moves to step 754. In step 754 the latest monitoring data for the selected evaluation parameter is compared for example to a long-term average, or conclusions are made using the neural network.

In step 755 a decision is made regarding whether a possible discovered difference between the latest location data and/or physiological measuring data and the long-term monitoring gives cause for an alarm to a monitoring party or not. If the difference value obtained as a result of the comparison reaches a pre-set threshold value, an alarm is not sent. The threshold value can be reached either by exceeding or falling below a threshold value set for a certain evaluation parameter. If several different physiological quantities are monitored, it is possible that the threshold value of one measured quantity being exceeded causes an alarm and the threshold value of another measured quantity being undercut causes an alarm. In an advantageous embodiment of the invention only the thresholds of several measured quantities being simultaneously unfulfilled in a predetermined manner causes an alarm.

In a situation without an alarm, the process moves to step 753, where the existing measuring data can be sent to the data processing device 34 which made the monitoring request. When the measuring data is sent, the process advances to step 76 in FIG. 6.

If a neural network is utilised in the decision-making in step 755, then the used neural network can be taught to give an alarm in step 755 when a certain combination of threshold vales set for the evaluation parameters is not fulfilled. The fulfilment of the threshold value can mean exceeding or falling under a threshold value of some pre-set physiological measurement, or different combinations of said threshold values in a certain interaction situation.

If it is as a final result of the comparison in step 755 found that the obtained difference value exceeds or falls under the threshold value set for at least one measurement parameter, an alarm is generated. In step 756, information regarding which evaluation parameter illustrating interaction or physiological measurements does not fulfill pre-determined limit values is added to the measuring data to be sent to the data processing device 34 which made the monitoring request. When the alarm is added to the measuring data to be sent, the process advances to step 76 in FIG. 6.

All the process steps of the monitoring of the activity illustrating interaction shown in FIGS. 5-7 can be implemented with computer program commands, which are performed in a suitable general-purpose processor or special-purpose processor. The computer program commands can be stored in a computer-readable media, such as a data disk or a memory, from where the processor can retrieve said computer program commands and implement them. The references to computer-readable media can for example also contain special components, such as programmable USB Flash memories, logic arrays (FPLA), application-specific integrated circuits (ASIC) and signal processors (DSP).

Some advantageous embodiments of the method and device according to the invention have been described above. The invention is not limited to the solutions described above, but the inventive idea can be applied in numerous ways within the scope of the claims. The invention is also not limited to the monitoring of the interaction of just one human and one pet, but instead of the pet there may also be two or more pets, the interaction of which in relation to the person or person is monitored either separately or together. In the same way there may be two or more companions, the interaction of who in relation to the monitored person is monitored either together or separately.

The invention claimed is:

1. A method for evaluating activity and functional ability of a living target via a data transfer network, which method comprises:
    measuring with a first wireless monitoring device in real-time activity data of a monitored first living target;
    storing the activity data of the first living target measured with the monitoring device into a database accessible via a data transfer network; and
    modifying from the activity data stored in the database an illustration of the activity of the first living target, which illustration can be presented via the data transfer network, which illustration is presented on a monitor of a data processing device;
wherein in order to evaluate the functional ability of the first living target, the method further comprises:
    measuring with a second wireless monitoring device in real-time activity data of a second living target;
    selecting at least one evaluation parameter illustrating interaction between the first living target and the second living target, which at least one evaluation parameter is used in evaluating activity and functional ability of the first living target and is included in the activity data of the first living target and the second living target;
    comparing short-term measuring data of the selected at least one evaluation parameter illustrating interaction between the first living target and the second living target to long-term corresponding measuring data of the selected at least one evaluation parameter; and
    sending based on the comparison information about a change in the activity and functional ability of the first living target to the data processing device, if a threshold value set for the selected at least one evaluation parameter illustrating the interaction is not fulfilled.

2. The method according to claim 1, wherein as the selected at least one evaluation parameter used in evaluating the activity and functional ability of the first living target is used, at least one of the following monitoring parameters included in the activity data of both the first living target and the second living target and related to interaction: travel path of the first living target, travel path of the second living target, movement speed, heart rate, EKG, EEG and EMG curves, body temperature, blood oxygen saturation, breathing sounds, speech volume, speech pitch, sound duration and frequency.

3. The method according to claim 2, wherein the measuring data of the selected at least one evaluation parameter illustrating interaction between the first living target and the second living target for a selected measuring time are compared to corresponding long-term average evaluation parameter values.

4. The method according to claim 2, wherein the measuring data of the selected at least one evaluation parameter illustrating interaction between the first living target and the second living target for the selected measuring time are analysed with a neural network, which has been taught corresponding physiological measuring signal values associated with common interactive events of the first living target and the second living target.

5. The method according to claim 1, wherein the first living target is a human or a pet and the second living target is a human.

6. An arrangement for evaluating activity and functional ability of a living target, the arrangement comprising:
an at least partly wireless data transfer network;
a first wireless monitoring device, which comprises means for determining a change in location data, activity data and physiological state data of a first living target in real-time and means for establishing a data transfer connection to a wireless data transfer network;
means for storing the location data, activity data and physiological state data of the first living target in a database accessible via the data transfer network; and
means for modifying the activity data stored in the database such that it is configured to be presented via the data transfer network and which is configured to be presented on a monitor of a data processing device, wherein the evaluation arrangement further comprises:
a second wireless monitoring device, which comprises means for determining a change in location data, activity data and physiological state data of a second living target in real-time and means for establishing a data transfer connection to the wireless data transfer network;
means for storing the location data, activity data and physiological state data of the second living target in the database accessible via the data transfer network;
means for selecting at least one evaluation parameter illustrating interaction between the first living target and the second living target, which at least one evaluation parameter is used in the evaluation of the activity and functional ability of the first living target;
means for comparing short-term measuring data of the selected at least one evaluation parameter illustrating interaction between the first living target and the second living target to corresponding long-term measuring data of the selected at least one evaluation parameter; and
means for sending information describing a change perceived based on the comparison in the activity and functional ability of the first living target to the data processing device, if a threshold value set for the selected at least one evaluation parameter illustrating the interaction is not fulfilled.

7. The arrangement for evaluating activity and functional ability according to claim 6, wherein the evaluation parameter used in the evaluation of the activity and functional ability of the first living target is at least one of the following monitoring parameters included in the activity data of both the first living target and the second living target and illustrating interaction: travel path of the first living target, travel path of the second living target, movement speed, heart rate, EKG, EEG and EMG curves, body temperature, blood oxygen saturation, breathing sounds, speech volume, speech pitch, sound duration and frequency.

8. The arrangement for evaluating activity and functional ability according to claim 7, wherein the measuring data of the selected at least one evaluation parameter illustrating interaction between the first living target and the second living target for a selected measuring time are configured to be compared to corresponding long-term average evaluation parameter values.

9. The arrangement for evaluating activity and functional ability according to claim 7, wherein the measuring data of the selected at least one evaluation parameter illustrating interaction between the first living target and the second living target for the selected measuring time are configured to be analysed with a neural network, which has been taught corresponding physiological measuring signal values associated with common interactive events of the first living target and the second living target.

10. The arrangement for evaluating activity and functional ability according to claim 6, wherein the first living target is a human or a pet and the second living target is a human.

11. A server, which comprises
means for receiving activity data sent from a monitoring device of a first living target which activity data comprises real-time location data of the first living target and at least one piece of data describing the functional ability of the first living target;
means for storing the received activity data into a database;
means for modifying the activity data stored in the database such that it is configured to be presented via a data transfer network and which is configured to be presented on a monitor of a data processing device, wherein the server further comprises:
means for receiving activity data sent from a monitoring device of a second living target, which activity data comprises real-time location data of the second living target and at least one piece of data describing the activity of the second living target;
means for selecting at least one evaluation parameter illustrating interaction between the first living target and the second living target, which at least one evaluation parameter is used in the evaluation of the activity and functional ability of the first living target;
means for comparing short-term measuring data of the selected at least one evaluation parameter illustrating interaction between the first living target and the second living target to corresponding long-term measuring data; and
means for sending information describing a change perceived based on the comparison in the activity and functional ability of the first living target to the data processing device, if a threshold value set for the selected at least one evaluation parameter illustrating the interaction is not fulfilled.

12. The server according to claim 11, wherein the selected at least one evaluation parameter used in the evaluation of the activity and functional ability of the first living target is at least one of the following monitoring parameters included in the activity data of both the first living target and the second living target: travel path of the first living target, travel path of the second living target, movement speed, heart rate, EKG, EEG and EMG curves, body temperature, blood oxygen saturation, breathing sounds, speech volume, speech pitch, sound duration and frequency.

13. The server according to claim 11, wherein the measuring data of the selected at least one evaluation parameter illustrating interaction between the first living target and the second living target for a selected measuring time are configured to be compared in the server to corresponding long-term average evaluation parameter values.

14. The server according to claim 11, wherein the measuring data of the selected at least one evaluation parameter illustrating interaction between the first living target and the second living target for the selected measuring time are configured to be analysed with a neural network included in the server, which neural network has been taught corresponding physiological measuring signal values associated with common interactive events of the first living target and the second living target.

15. The server according to claim 11, wherein the first living target is a human or a pet and the second living target is a human.

16. A computer program product that comprises computer program code stored on a non-transitory computer-readable medium, which computer program code is configured to execute the following steps when said computer program code is executed on a computer:

measuring with a first wireless monitoring device in real-time activity data of a monitored first living target;

storing the activity data of the first living target measured with the monitoring device into a database accessible via a data transfer network; and modifying from the activity data stored in the database an illustration of the activity of the first living target, which illustration can be presented via the data transfer network, which illustration is presented on a monitor of a data processing device, wherein in order to evaluate the functional ability of the first living target, the method further comprises:

measuring with a second wireless monitoring device in real-time activity data of a second living target;

selecting at least one evaluation parameter illustrating interaction between the first living target and the second living target, which at least one evaluation parameter is used in evaluating activity and functional ability of the first living target and is included in the activity data of the first living target and the second living target;

comparing short-term measuring data of the selected at least one evaluation parameter illustrating interaction between the first living target and the second living target to long-term corresponding measuring data of the selected at least one evaluation parameter; and sending based on the comparison information about a change in the activity and functional ability of the first living target to the data processing device, if a threshold value set for the selected at least one evaluation parameter illustrating the interaction is not fulfilled;

wherein as the selected at least one evaluation parameter used in evaluating of the activity and functional ability of the first living target is used, at least one of the following monitoring parameters included in the activity data of both the first living target and the second living target and related to interaction: travel path of the first living target, travel path of the second living target, movement speed, heart rate, EKG, EEG and EMG curves, body temperature, blood oxygen saturation, breathing sounds, speech volume, speech pitch, sound duration and frequency;

wherein the measuring data of the selected at least one evaluation parameter illustrating interaction between the first living target and the second living target for a selected measuring time are compared to corresponding long-term average evaluation parameter values;

wherein the measuring data of the selected at least one evaluation parameter illustrating interaction between the first living target and the second living target for the selected measuring time are analysed with a neural network, which has been taught corresponding physiological measuring signal values associated with common interactive events of the first living target and the second living target; and wherein the first living target is a human or a pet and the second living target is a human.

* * * * *